United States Patent
Krimsky et al.

(10) Patent No.: US 11,058,454 B2
(45) Date of Patent: Jul. 13, 2021

(54) DEVICE FOR MEDICAL PROCEDURE LOCALIZATION AND/OR INSERTION

(71) Applicant: InnoVital, LLC, Calverton, MD (US)

(72) Inventors: William Sanford Krimsky, Forest Hill, MD (US); Curt Steven Kothera, Crofton, MD (US); Amit Navin Shah, Bethesda, MD (US); Gregory John Hiemenz, Silver Spring, MD (US)

(73) Assignee: InnoVital, LLC, Calverton, MD (US)

( * ) Notice: Subject to any disclaimer, the term of this patent is extended or adjusted under 35 U.S.C. 154(b) by 310 days.

(21) Appl. No.: 16/378,048

(22) Filed: Apr. 8, 2019

(65) Prior Publication Data

US 2020/0100809 A1 Apr. 2, 2020

Related U.S. Application Data

(63) Continuation of application No. 15/545,797, filed as application No. PCT/US2016/014250 on Jan. 21, 2016, now Pat. No. 10,595,898, application No. 16/378,048, which is a continuation of application No. 15/024,832, filed as application No. PCT/US2014/057717 on Sep. 26, 2014, now Pat. No. 10,758,695.

(51) Int. Cl.
 A61B 17/34 (2006.01)
 A61M 16/04 (2006.01)
 A61M 27/00 (2006.01)

(52) U.S. Cl.
 CPC ..... *A61B 17/3403* (2013.01); *A61M 16/0488* (2013.01); *A61M 27/002* (2013.01)

(58) Field of Classification Search
 CPC ............ A61B 17/3403; A61M 27/002; A61M 16/0488
 See application file for complete search history.

(56) References Cited

U.S. PATENT DOCUMENTS 3,791,386 A * 2/1974 McDonald ........ A61M 16/0472
128/207.29

* cited by examiner

*Primary Examiner* — Amber R Stiles
(74) *Attorney, Agent, or Firm* — Royal W. Craig; Gordon Feinblatt LLC

(57) ABSTRACT

A device (100) for medical procedure localization that provides a template that indexes the site of interest along a first axis or plane that is defined by anatomical landmarks of a patient. An embodiment is disclosed in which a first axis is an axillary line from the patient's axilla (armpit) toward the iliac crest (pelvis) and the site of interest is a distance away from the axilla along said first axis. The site of interest is the 3rd, $4^{th}$ or $5^{th}$ intercostal space, into which a needle/catheter and/or chest tube may be placed for decompression.

38 Claims, 2 Drawing Sheets

DEVICE FOR MEDICAL PROCEDURE LOCALIZATION AND/OR INSERTION

CROSS-REFERENCE TO RELATED APPLICATION(S)

The present application is a continuation of U.S. application Ser. No. 15/545,797 which is a national entry of PCT application No. PCT/US16/14250 filed 21 Jan. 2016, and is a continuation of U.S. Ser. No. 15/024,832 filed 24 March 2016, which is a national entry of PCT application no. PCT/US14/57717 filed 26 Sep. 2014, which in turn derives priority from U.S. provisional application Ser. No. 62/106,403 filed 22 Jan. 2015.

BACKGROUND OF THE INVENTION

1. Field of the Invention

The present invention generally relates to medical devices for performing medical procedures, such as chest decompression and/or drainage, thoracentesis, thoracostomy, or the like and, more particularly, to an assist device using anatomical landmarks to pinpoint the procedure site. In one embodiment, a chest decompression assist device is disclosed for the drainage of air and/or fluid from the chest.

2. Description of Prior Art

Studies suggest that many wartime casualties could be avoided if interim tools and procedures could be implemented to allow non-experts to more accurately perform certain procedures before the injured patient can be transported to a higher level of care facility. For example, tension pneumothorax (collapsed lung) is among the top three causes of preventable combat death. Eastridge, Brian et al., "*Death on the Battlefield* (2001-2011): *Implications For The Future Of Combat Casualty Care*, Journal of Trauma and Acute Care Surgery, Volume 73, Issue 6, pp S431-S437 (December 2012). This is because the remedial procedure is often performed incorrectly.

That procedure is a needle decompression effected by insertion of an intercostal catheter (ICC). The ICC requires a "thoracostomy", a small incision of the chest wall, with maintenance of the opening for drainage. The drainage is accomplished by use of a catheter/needle or a thoracostomy tube (insertion of a chest tube into the pleural cavity), in to drain pleural contents such as air or blood.

A needle thoracostomy involves needle placement into the affected side of the chest, often with an anterior approach at the second intercostal space in the mid-clavicular line, just above the rib to avoid the intercostal nerves and vessels. Once the needle is placed, a catheter is inserted over the needle. Alternatively, the lateral approach at the third, fourth or fifth intercostal space along the anterior axillary line or mid-axillary line is an accepted site. Chest tube decompression (also known as "tube thoracostomy") involves placement of a tube through the chest wall into the pleural cavity primarily to drain an air or fluid collection from the pleural space. Chest tubes are typically placed laterally.

Assuming a needle decompression in the midclavicular line in the second intercostal space which is just above the third rib, location entails identifying the third rib, and then following it out to the midclavicular line to locate the site for needle decompression. That is difficult enough for trained surgeons. The problem is exacerbated on the battlefield because the procedure may need to be performed by combat medics or fellow soldiers under duress and body armor must be removed. Thoracic injuries occurred in nearly 10% of wounded personnel in recent military engagements. Ivey, K. M., et al., 2012, "*Thoracic injuries in US combat casualties: a* 10-*year review of Operation Enduring Freedom and Iraqi Freedom*", Journal of Trauma Acute Care Surgery, 73(6 Suppl 5): S514-S519. Tension pneumothorax, a consequence of thoracic trauma, is among the top three causes of preventable combat death. Eastridge, Brian et al., "*Death on the Battlefield* (2001-2011): *Implications For The Future Of Combat Casualty Care*, Journal of Trauma and Acute Care Surgery, Volume 73, Issue 6, pp S431-S437 (Dec. 2012). Battlefield factors include limited training and experience of combat medics relative to physicians, and the battlefield environment itself. It has been shown, for example, that stressful conditions can adversely affect clinical skill. Moorthy, K., Munz, Y., Dosis, A., Bannm, S., Darzi, A., "*The Effect Of Stress-Inducing Conditions On The Performance Of A Laparoscopic Task*", Surgical Endoscopy, 17(9): 1481-1484 (2003).

It has been reported that failures occur in 30-50% of cases. Barton E D et al., *Prehospital Needle Aspiration And Tube Thoracostomy In Trauma Victims: A Six-Year Experience With Aeromedical Crews*, Journal of Emergency Medicine (1995); Ball C. et al., "*Thoracic Needle Decompression For Tension Pneumothorax: Clinical Correlation With Catheter Length*" Canadian Journal of Surgery, 53: 184-188 (2010); Davis D P et al., *The Safety And Efficacy Of Prehospital Needle And Tube Thoracostomy By Aeromedical Personnel*, Prehospital Emergency Care, 9: 191-197 (2005). Major reasons for failure include incorrect needle and/or chest tube location. Netto F A et al., "*Are needle decompressions for tension pneumothraces being performed appropriately for appropriate indications?*", American Journal of Emergency Medicine 26:597-602 (2008). Aylwin, C. J., 2008, "*Pre-Hospital and In-Hospital Thoracostomy: Indications and Complications*", Annals of the Royal College of Surgeons of England, 90(1): 54-57.

There are prior art chest decompression devices/kits available, but they still rely on the user to identify subtle surface anatomical landmarks, and to use these landmarks to insert the needle/catheter. Hence, they do not address the problems of untrained identification under duress.

A simplified and more reliable procedure is imperative. Several kits have been developed in an attempt to simplify the procedures or reduce the number of tools needed, but none have demonstrated statistically significant improvement in terms of factors such as time to completion, accuracy in placing catheter, and complication rates. This is because the developed kits still rely on the user to find and use the proper anatomical landmarks during insertion.

What is needed is an assist device for guiding percutaneous access, particularly for chest decompression, that significantly improves the success rate and effectiveness of performing the procedures.

SUMMARY OF THE INVENTION

In accordance with the foregoing objects, it is an object of the present invention to provide a device for guiding localization and insertion of a needle or tube for chest decompression that is easy-to-use, designed with simplifying features to avoid both common and devastating errors (or at least features that significantly reduce the chance of such errors to occur), and that is effective and broadly applicable.

It is another object to provide a device for localization of an insertion point for a needle or tube that uses physical reference points of the anatomy (i.e., anatomical landmarks) for alignment and instrument placement.

It is another object to provide a device for medical procedure localization and/or insertion that may be used by both skilled and unskilled personnel.

In accordance with the foregoing and other objects, the present invention is a device for medical procedure localization and/or insertion that provides a percutaneous access template that is easily aligned with blatant physical reference points of the anatomy (i.e., anatomical landmarks), and which thereby positions a window (i.e., target safe zone) for accurate localization and insertion of a needle or tube for chest decompression. The template (described below) enables accurate identification of the proper landmarks to improve efficacy of the procedures, and to make incorrect performance difficult.

BRIEF DESCRIPTION OF THE DRAWINGS

Other objects, features, and advantages of the present invention will become more apparent from the following detailed description of the preferred embodiments and certain modifications thereof when taken together with the accompanying drawings in which.

DETAILED DESCRIPTION OF THE PREFERRED EMBODIMENTS

The present invention is a procedural assist device that improves the safety and effectiveness of certain medical procedures using anatomical landmarks to pinpoint the procedure site. The device provides a percutaneous access template that is easily aligned with pronounced physical reference points of the anatomy (i.e., anatomical landmarks), and which thereby positions a window for accurate siting of a thoracostomy (creation of a hole in the chest wall) and/or placement of a thoracostomy device (herein defined as a needle, catheter, chest tube, guidewire, or dilator into the pleural cavity. Though the insertion may be for any "site-specific procedure", the present device is particularly well-suited for reliably identifying the site of interest for needle/chest decompression. Thus, a first embodiment of the invention is herein described in the context of a device suited for chest decompression by needle/catheter insertion at the 3rd, 4th or 5th intercostal space along the anterior axillary line of the patient, where the catheter generally fits tightly over the needle, effectively as a single instrument. Then during the procedure, the needle is used to pierce the tissue and enter the pleural space first, after which it is removed, leaving the catheter in place.

In this context the device provides an insertion template that uses one geometrical feature to reference one anatomical landmark and a second geometrical feature to reference a second anatomical landmark, thereby allowing orientation of the insertion template along a first axis. A fixed distance from one of said geometrical features and along said first axis is an opening or window that identifies the site of interest (i.e., safe zone) for the procedure. The first axis is parallel to the (anterior) axillary line from the patient's axilla (armpit) and directed towards the iliac crest (pelvis). The window identifies the 3rd, $4^{th}$ or $5^{th}$ intercostal space, into which the instrument (needle/catheter) is to be placed to properly accomplish the procedure (decompression). Note that in this application, the positioned device forms a plane and can be used as a guide for the user during instrument insertion, which is generally perpendicular to the device plane.

Figure 1:
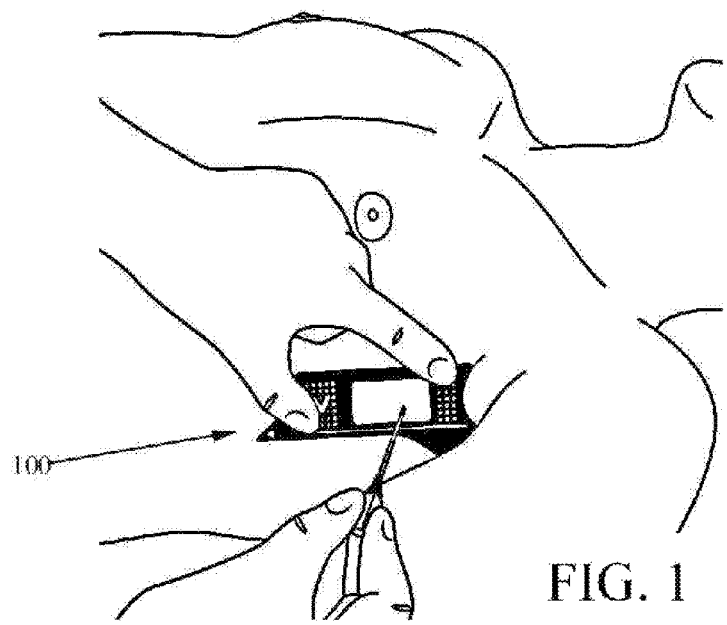
FIG. 1 is a front perspective illustration of a preferred embodiment of the device 100 for medical procedure localization and/or insertion shown during use for a procedure on the patient's left side (e.g., needle or chest decompression).
Figure 2:
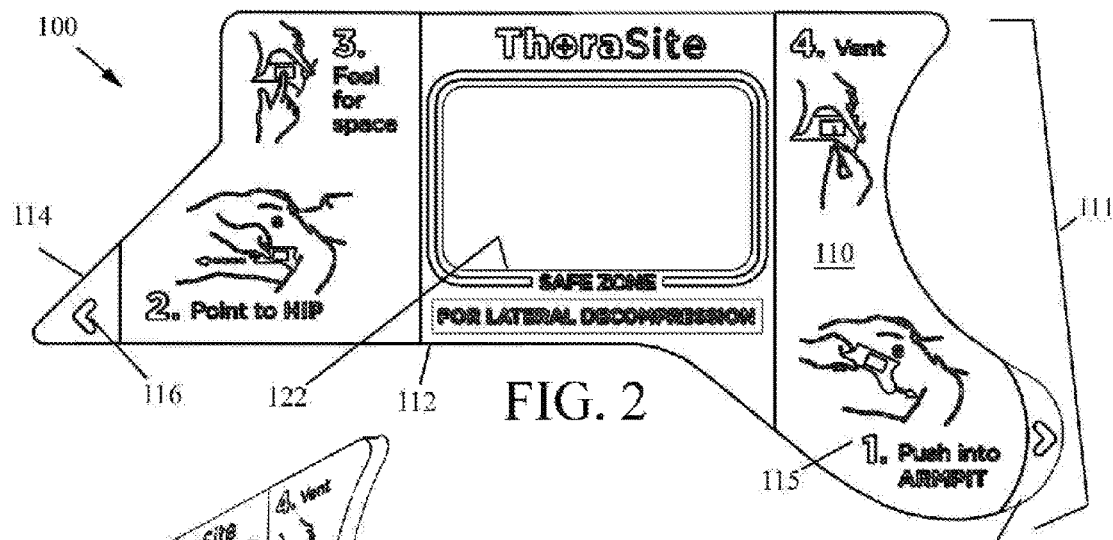
FIG. 2 is an enlarged front view of the device 100 of FIG. 1.
Figure 3:
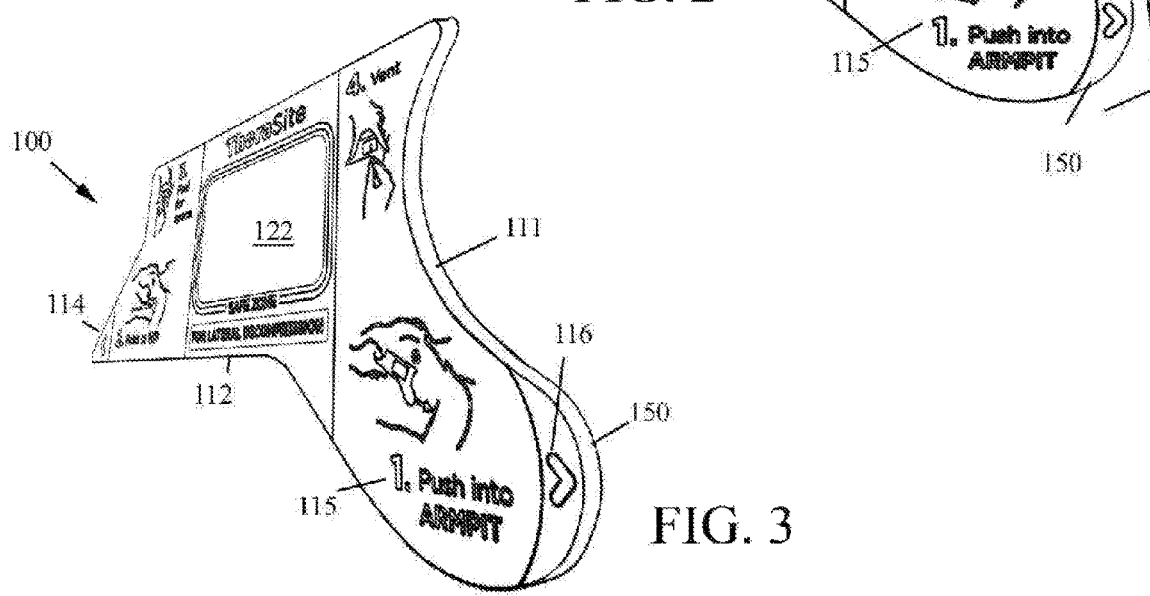
FIG. 3 is a side perspective view of the device 100 of FIGS. 1-2.

As seen in FIGS. 1-3, the device 100 for medical procedure localization and/or insertion generally comprises a flat planar base component 110 which may be molded or cut from an elastically resilient sheet material such as plastic sheet. It may alternatively be formed from one or more layers in a laminate structure. The base component 110 defines an elongate two-dimensional geometric shape with an open needle placement window 122 through the shape. Though the illustrated embodiment shows window 122 completely bounded, one skilled in the art will understand that the base component 110 may provide a slot or channel from the window to the edge through which a needle/catheter can pass, thereby allowing sidelong removal of the base component 110 from the procedure site. The geometric shape may be substantially rectangular and, in any case, extends end-to-end, with an axilla locator 111 at one end and an iliac crest pointer 114 at the other end.

The axilla locator 111 minimally comprises a superior arch segment configured, for example, as a substantially circular segment bounded by an inwardly facing arch or other concave edge to reference and identify the anatomical shape of the anterior axillary fold of the patient. The axilla locator 111 more preferably comprises a curvilinear outwardly-directed protuberance or "dorsal extension" 150 at the superior edge (as shown) that presents a more pronounced and extended curvilinear notch. The outwardly-directed axillary extension or protuberance is for insertion in the patient's axilla, while the extended curvilinear notch is for indexing against said patient's anterior axillary fold. Axilla locator 111 therefore defines the superior end-point of the first axis defined by the device 100.

Base 110 extends lengthwise from axilla locator 111 in the inferior direction along extension 112 to iliac crest pointer 114 at the other end. The iliac crest pointer 114 may be any single-directionally-oriented geometric feature extending from an end of base 110, but is most preferably a right triangle aligned with the edge of extension 112 as this geometry offers a most self-evident and visually accurate alignment mechanism (e.g., the top half of an arrowhead) that preferentially provides a quick alignment facility pointing the device 100 towards the patient's iliac crest, thereby orienting window 122 along the anterior axillary line (from the patient's axilla towards the iliac crest when the axilla locator 111 is indexed against said patient's axillary fold). Aligning pointer 114 with the iliac crest therefore defines the inferior end-point of the first axis defined by said device 100. Optimally the device 100 should be pointed between the anterior border (anterior superior iliac spine or "ASIS") and posterior border (posterior superior iliac spine or "PSIS") of the iliac crest, about a third of the way back from the ASIS, roughly at the iliac tubercle. To achieve greater accuracy the inferior edge of extension 112 may additionally or alternately reference an axis of the patient's thorax (axis of back or spine).

Figure 4:
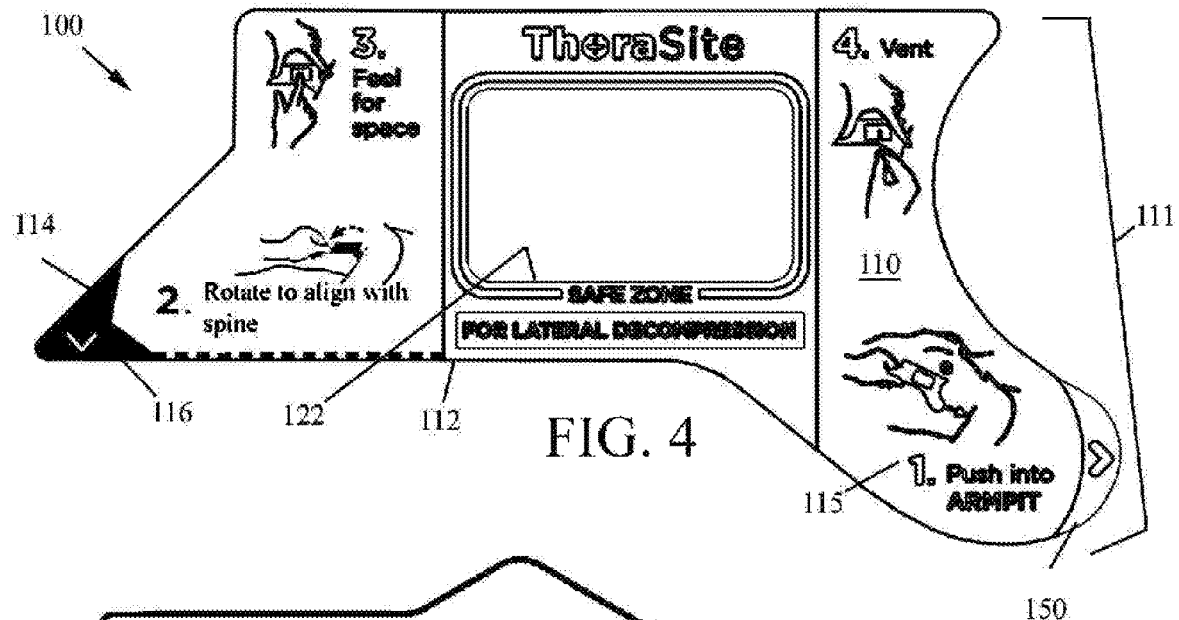
FIG. 4 is a side perspective view of the device 100 with alternate indicia for rotating the device 100 until a dotted straight line is aligned with the patient's spine.

FIG. 4 illustrates an embodiment where a downward arrow suggests rotating the device 100 until a dotted straight line is aligned with an axis of the patient's thorax (axis of back or spine). Note that in this context back and spine are generally used interchangeably and meant to describe an axis of the patient's thorax. This likewise indexes orientation of the locator template 100 along an axillary line from the patient's axilla toward the iliac crest when said first locator feature is indexed against said patient's axillary fold.

Inferior extension 112 of base 110 contains an opening that defines window 122 that demarcates the procedure area "safe zone." Optimally the ventral side of the window 122 (i.e., the top margin closest to the front of the body) falls along a line parallel to the anterior axillary line (AAL), while dorsal side of the window 122 (i.e., the bottom margin in the figures) falls along a line parallel to the mid-axillary line (MAL) (the MAL and AAL being parallel). Thus, a first axis is defined by the two anatomical landmarks identified by features 111 and 114. During use, iliac crest pointer 114 is pointed generally toward the patient's iliac crest (i.e., pelvis), and more preferably between the anterior border (anterior superior iliac spine or "ASIS") and posterior border (posterior superior iliac spineor "PSIS") of the iliac crest, about a third of the way back from the ASIS, roughly at the iliac tubercle. This serves as a second anatomical reference point to ensure proper alignment of device 100 (i.e., defining the first axis—the axillary line or anterior axillary line).

To provide the user with information on correct orientation of device 100 relative to the patient, base component 110 preferably comprise stepwise descriptive annotations 115 reflecting a method of using the present invention, such as "1: push into armpit", "2: point to hip"; "3: feel for (intercostal) space"; "4: vent", and "safe zone" (for the needle). Further, base 110 may feature geometrical shapes 116 that provide guidance to the user on correct device orientation and/or usage. Base 110 is also preferably asymmetric about the coronal plane to prevent incorrect usage. Preferable examples of such asymmetry are iliac crest pointer 114 at the inferior edge and dorsal extension 150 at the superior edge.

The annotations 115 of base component 110 preferably appear on both lateral faces of base 110 because it must be applicable (annotations visible to user) when placed on either the left or right side of the patient (e.g., symmetric about sagittal plane) for the exemplary procedure of chest decompression, though this is not necessary for all procedures.

With base component 110 positioned to provide anatomical references for the first axis or plane (axillary line) from the patient's axilla/anterior axillary fold toward the iliac crest, window 122 defines the procedure area and is sized such that intercostal spaces appearing therewithin are acceptable procedure locations on the patient. The user simply palpates in window 122 to identify an intercostal space and inserts the instrument preferably superior to the rib to accomplish decompression. It is understood that different intercostal spaces may be identified in patients of different heights, but a range of intercostal spaces are acceptable locations (e.g., $3^{rd}$ to $5^{th}$) for lateral chest decompression, and anthropometric data has been used to size window 122 and locate it relative to the axilla, accordingly. The design has been validated through testing across a range of patient heights and body mass indices. Shah A N, Kothera C S, Dheer S. 2019, *ThoraSite: A Device to Improve Accuracy of Lateral Decompression Needle and Chest Tube Placement*, J Trauma Acute Care Surg. (2019).

A procedure for use of this single component device 100 for localization and/or insertion comprises the following steps (demonstrated by indicia 115):

1. Place axilla locator 111 of base component 110 in patient's anterior axillary fold; dorsal extension 150 will be in patient's axilla (armpit).
2. Position iliac crest pointer 114 of base component 110 toward the iliac crest (pelvis or hip bone), such that said pointer is generally directed to iliac tubercle. Alternately or additionally, rotate the device 100 in accordance with FIG. 4 (step 2) until the dotted straight line is aligned with the patient's spine/back.
3. Palpate within window 122 to find an intercostal space of patient.
4. Insert needle in intercostal space inside window 122 above the rib to accomplish decompression.

The foregoing is far simpler and less error prone than using a freehanded approach (i.e., using one's fingers alone) to locate an anterior or lateral decompression site.

It should also be noted that a similar single component device 100 may also be used to accomplish chest decompression through the anterior approach, where base 110 references the patient's clavicle and uses the pointer 114 to help the user identify the mid-clavicular line (e.g., pointer oriented toward the sternum). In this instance, window 122 is sized for an acceptable range of anterior intercostal spaces (e.g., $2^{nd}$ or $3^{rd}$).

In an alternate embodiment, device 100 may be adapted to enable conversion from a more temporary medical instrument to a more durable medical instrument or medical device such as, but not limited to, conversion from a decompression catheter to a chest tube or from a cricothyrotomy tube to a tracheostomy tube. Depending on the medical procedure of interest, this conversion may be via the procedure site identified by device 100 through the window 122, or via a second procedure site referenced from the first procedure site. For example, a decompression needle/catheter and chest tube may both be placed in the $4^{th}$ or $5^{th}$ intercostal space along the anterior axillary line, whereas a cricothyrotomy tube and tracheotomy tube are placed in different procedure sites, both of which are referenced from many of the same anatomical landmarks.

It should now be apparent that the device for assisting percutaneous procedures described above will significantly improve the success rate and effectiveness of performing the relevant procedure. Device 100 mimics an expert medical approach, yet decreases the skill level necessary to perform procedure via geometric features for foolproof, bilateral use and annotations for user orientation and instruction.

The above-described device may also be used in preparation for percutaneous procedures or alternatively to train for such procedures. For example, a medic or other potential care provider may wish to practice the procedure using device 100 and remove mental roadblocks to initiating a necessary procedure (i.e., place device 100 on the chest of a mock patient and simulate needle decompression with a straw). Alternatively, a medic may wish to pre-size each of his/her soldiers for the relevant procedure and/or use device 100 to make a mark on a patient (i.e., using a marker to outline the procedure site and then put the device aside and perform the chest decompression if needed). Those skilled in the art will appreciate that various anatomic landmarks may be used to place drains in the chest for distinct purposes. Non-limiting examples include the mid-clavicular line for anterior chest drainage and anterior axillary or mid-axillary lines for lateral chest drainage. Posterior chest drainage may also be accomplished with such a device through the use of surface anatomical landmarks.

Those skilled in the art will appreciate that the surfaces or distinct regions on the surfaces of base component 110 need not be entirely flat, continuous material. For example, texture can be added to the surfaces to enhance handling of the device 100, particularly in scenarios where fluids are present. For example, regions of base 110 can be accented with one or more perforations or small holes for grip enhancement or even to aid the user with instructions for device 100 usage (see FIG. 6 and description below).

Figure 5:
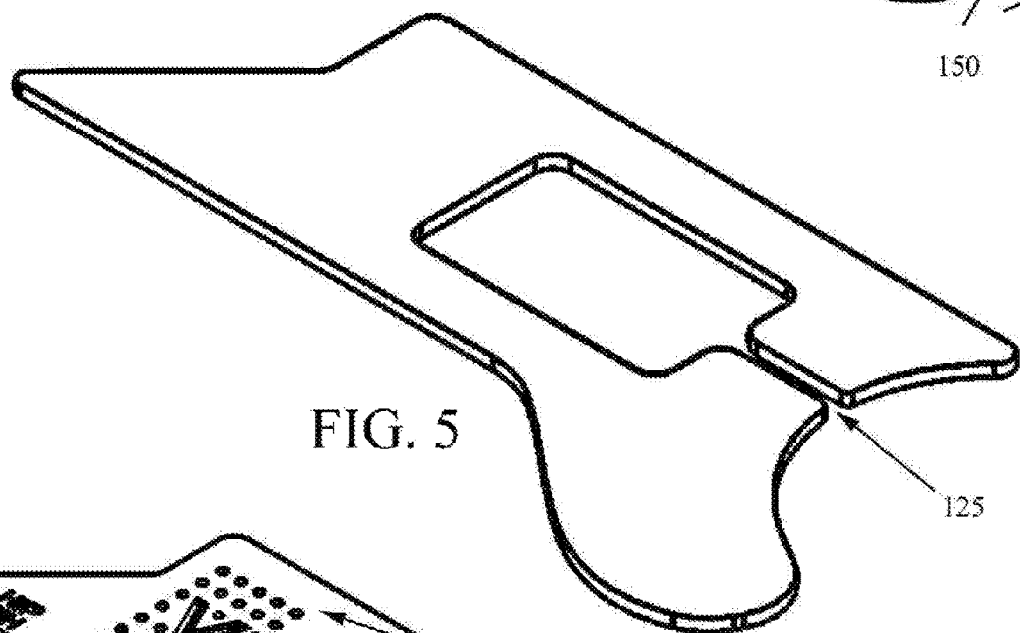
FIG. 5 is a side perspective view of the device 100 in which base 110 is defined by a slot 125 into window to allow sidelong removal of the base component 110 from the procedure site (needle/catheter passing through slot 125).

FIG. 5 shows an example in which base 110 is defined by a slot 125 into window to allow sidelong removal of the base component 110 from the procedure site (needle/catheter passing through slot 125).

Figure 6:
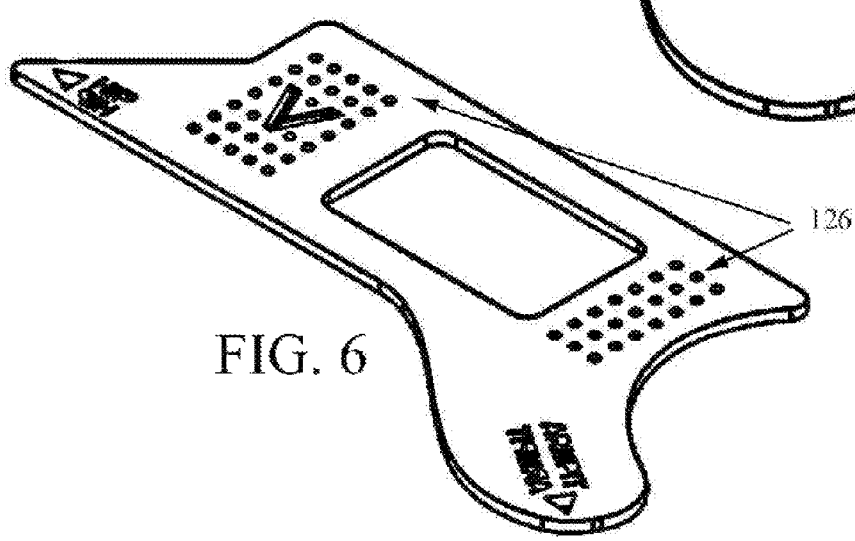
FIG. 6 is a side perspective view of the device 100 in which base 110 is defined by a pattern of perforations 126 for grip enhancement.

FIG. 6 shows an example in which base 110 is defined by a pattern of perforations 126 for grip enhancement.

The base component 110 should have a flexural rigidity high enough such that, when placing the dorsal extension 150 into the patient's axilla, it does not bend or buckle. Flexural rigidity is defined as the resistance offered by a structure when undergoing bending and is calculated as the product of the material's Young's modulus, E, and the second moment of area, I, of the structure. The flexural rigidity, or EI, of a structure is also proportional to the structure's buckling strength. The preferred flexural rigidity of the base component is greater than or equal to 400 Newtons×millimeter×millimeter [Newtons×mm$^2$]. Since the second moment of interia, I, of a structure is proportional to the cube of the thickness, the thickness of the base component 110 heavily contributes to its flexural rigidity. For common materials, a thickness of greater than or equal to 0.15 millimeters is preferred for the base component 110.

Having now fully set forth the preferred embodiment and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

What is claimed is:

1. A locator template for indexing a thoracostomy site on a human patient, comprising a flat elongate base extending from a first end to a second end, and shaped with,
   a first locator feature at the first end configured to index a position of said locator template relative to the patient's axilla,
   a second locator feature distinct from said first locator feature and configured to index orientation of said locator template relative to at least one anatomical landmark by alignment with said anatomical landmark; and
   a window through said flat elongate base between said first end and second end that frames at least one of said patient's intercostal spaces along an axillary line.

2. The locator template according to claim 1, wherein a procedure site marks placement of an instrument into said human patient's pleural space.

3. The locator template according to claim 1, wherein said first locator feature at the first end comprises a curvilinear notch configured for seating against said patient's axillary fold.

4. The locator template according to claim 3, wherein said second locator feature at the second end further comprises a directional pointer to index orientation of said locator template.

5. The locator template according to claim 4, wherein said second locator feature at the second end further comprises a protruding triangle.

6. The locator template according to claim 5, wherein said protruding triangle is a protruding right triangle.

7. The locator template according to claim 4, wherein said second locator feature at the second end points at any one from among a group consisting of said patient's pelvis, hip, knee, or leg.

8. The locator template according to claim 7, wherein when said second locator feature is pointed at said patient's hip, said locator template indexes orientation of said locator template along an axillary line from the patient's axilla to the patient's iliac crest when said first locator feature is indexed against said patient's axillary fold.

9. The locator template according to claim 3, wherein said second locator feature at the second end further comprises a linear marking to index orientation of said locator template to an axis of the patient's thorax.

10. The locator template according to claim 9, wherein when said second locator feature is aligned with said axis of the patient's thorax, said locator template indexes orientation of said locator template substantially along an axillary line from the patient's axilla to the patient's iliac crest when said first locator feature is indexed against said patient's axillary fold.

11. The locator template according to claim 1, wherein said first locator feature at the first end comprises an outwardly-directed protruberance for insertion in said patient's axilla.

12. The locator template according to claim 11, further comprising first indicia proximate said first locator feature for instructing a user to seat said outwardly directed protruberance of said first locator feature against said patient's axilla such that said first locator feature abuts said patient's axillary fold.

13. The locator template according to claim 12, further comprising second indicia proximate said second locator feature for assisting a user to use said second locator.

14. The locator template according to claim 13, further comprising third indicia proximate said window for instructing a user to feel for said patient's intercostal space within said window.

15. The locator template according to claim 1, wherein said window is substantially rectangular.

16. The locator template according to claim 1, wherein said base comprises a flat resilient sheet material.

17. The locator template of claim 1, wherein said flat elongate base further comprises at least one textured surface.

18. The locator template of claim 1, wherein said flat elongate base further comprises at least one perforation therethrough other than said window.

19. The locator template of claim 1, wherein said window is not completely bounded within said base, and instead has an opening at least as wide as an instrument used for a procedure to pass therethrough.

20. A device for assisting medical procedures, comprising:

a flat elongate base extending from a first end to a second end;

a first locator feature at the first end of said base configured to index said device to an anatomical landmark at said first end;

a second locator feature spaced from said first locator feature and configured to index said device to a second anatomical landmark at said second end; and a third locator feature between said first locator feature and said second locator feature that identifies a procedure site, wherein said medical procedure is a thoracostomy.

21. The device according to claim 20, wherein said first locator feature at the first end is configured to index a position of said device relative to a patient's axilla.

22. The device according to claim 21, wherein said second locator feature is configured to index orientation of said device relative to at least one anatomical landmark by alignment with said at least one anatomical landmark.

23. The device according to claim 22, wherein said second locator feature at the second end is configured to point said device at the patient's iliac crest.

24. The device according to claim 21, wherein said first locator feature at the first end comprises a curvilinear notch configured for seating against said patient's axillary fold.

25. The device according to claim 24, wherein said first locator feature at the first end further comprises an outwardly-directed protuberance for insertion in said patient's axilla.

26. The device according to claim 24, wherein said second locator feature further comprises a directional pointer to index orientation of said device.

27. The device according to claim 26, wherein said second locator feature further comprises a protruding triangle.

28. The device according to claim 26, wherein when said second locator feature is pointed at said patient's iliac crest, said device indexes orientation of said device along an axillary line from the patient's axilla to the patient's iliac crest when said first locator feature is indexed against said patient's axilla.

29. The device according to claim 28, further comprising first indicia proximate said first locator feature for instructing a user to seat said outwardly directed protuberance of said first locator feature into said patient's axilla, second indicia proximate said second locator feature for instructing the user how to use said second locator feature, and third indicia proximate said window for instructing the user to feel for said patient's intercostal space within said window.

30. The device according to claim 24, wherein said second locator feature further comprises a line for aligning with an axis of the patient's thorax to index orientation or said device.

31. The device according to claim 30, wherein when said second locator feature is aligned with said patient's spine, said device indexes orientation of said device along an axillary line from the patient's axilla to the patient's iliac crest when said first locator feature is indexed against said patient's axilla.

32. The device according to claim 20, wherein said third locator feature comprises a window through said flat elongate base between said first end and second end for framing at least one of a patient's intercostal spaces along an axillary line.

33. A medical procedure template comprising a base extending from a first end to a second end, a first locator feature at the first end of said base configured to index said procedure template to a first anatomical landmark at said first end, a second locator feature spaced from said first locator feature and configured to index said procedure template to a second anatomical landmark, and a third locator feature comprising a window through said base that frames a medical procedure site.

34. The medical procedure template according to claim 33, wherein a medical procedure is a thoracostomy.

35. The medical procedure template according to claim 34, wherein said first locator feature at the first end is configured to index a position of said procedure template relative to the patient's axilla.

36. The medical procedure template according to claim 35, wherein said second locator feature is configured to index orientation of said procedure template relative to at least one anatomical landmark by alignment with said at least one anatomical landmark.

37. The locator template of claim 33, wherein said base has a thickness greater than or equal to 0.15 millimeters.

38. The locator template of claim 33, wherein said base has a flexural rigidity greater than or equal to 400 Newtons×mm$^2$.

* * * * *